US00PP20379P2

(12) United States Plant Patent
McCracken

(10) Patent No.: US PP20,379 P2
(45) Date of Patent: Oct. 6, 2009

(54) ***LIGUSTRUM* PLANT NAMED 'SUNSHINE'**

(50) Latin Name: *Ligustrum sinense*
Varietal Denomination: Sunshine

(76) Inventor: Thomas P. McCracken, 8025 Fowler Rd., Zebulon, NC (US) 27597

( * ) Notice: Subject to any disclaimer, the term of this patent is extended or adjusted under 35 U.S.C. 154(b) by 286 days.

(21) Appl. No.: 11/784,920

(22) Filed: Apr. 10, 2007

(51) Int. Cl.
*A01H 5/00* (2006.01)

(52) U.S. Cl. ..... Plt./336

(58) Field of Classification Search ..... Plt./336
See application file for complete search history.

*Primary Examiner*—Annette H Para
(74) *Attorney, Agent, or Firm*—Audrey Charles

(57) ABSTRACT

A new and distinct cultivar of *Ligustrum* plant named 'Sunshine', characterized by its mixture of yellow green and medium green-colored growing season foliage, lack of flower production, and compact growth habit.

1 Drawing Sheet

Latin name of genus and species of plant claimed: *Ligustrum sinense.*

Variety denomination: 'Sunshine'.

BACKGROUND OF THE INVENTION

The present invention relates to a new and distinct cultivar of *Ligustrum* plant botanically known as *Ligustrum sinense* and hereinafter referred to by the cultivar name 'Sunshine'.

The new cultivar selected by the inventor originated in a controlled selection program in Zebulon, N.C. during 2002.

The new *Ligustrum* cultivar is a naturally occurring sport of an unnamed *Ligustrum sinense* characterized by its medium green-colored growing season foliage, flower and fruit production, and dense thicket-like growth habit. The new cultivar was discovered as a branch sport and selected in July 2002 in an outdoor, commercial nursery located in Zebulon, N.C.

Asexual reproduction of the new cultivar by terminal stem cuttings since July 2002 at McCracken Nursery, Zebulon, N.C. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Sunshine' as a new and distinct cultivar of *Ligustrum* plant:

1. A mixture of yellow green and medium green-colored growing season foliage;
2. Lack of flower production; and
3. Compact growth habit.

Plants of the new cultivar differ from plants of the parent primarily in foliage coloration and sterility.

Of the many commercially available *Ligustrum sinense* known to the inventor, the most similar in comparison to the new cultivar is the unnamed parent *Ligustrum sinense*. However, in side by side comparisons, plants of the new cultivar differ from plants of *Ligustrum sinense* in the following characteristics:

1. Plants of the new cultivar have a mixture of yellow green and medium green-colored growing season foliage, while the plants of *Ligustrum sinense* have medium green-colored growing season foliage; and 2. Plants of the new cultivar are sterile, while plants of *Ligustrum sinense* bare flowers and fruit.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Sunshine'. The plants were grown in a landscape setting for five years in Zebulon, N.C.

DETAILED BOTANICAL DESCRIPTION

Figure 1:
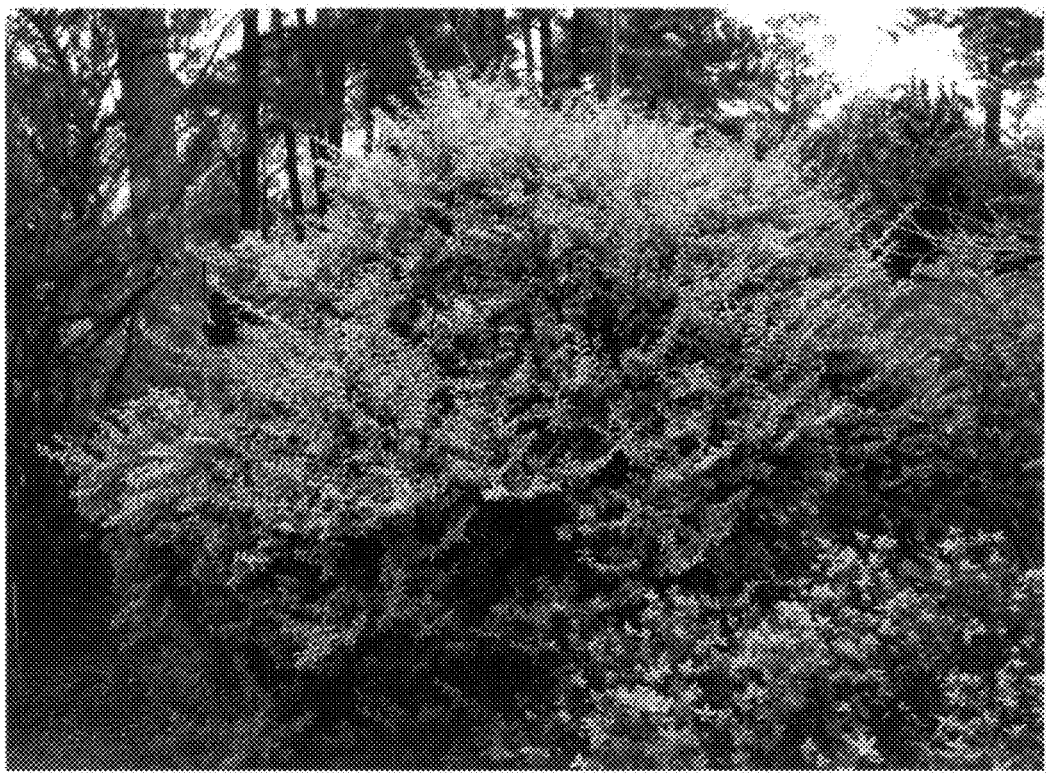
FIG. 1 illustrates the overall growth and habit of 'Sunshine'.
Figure 2:
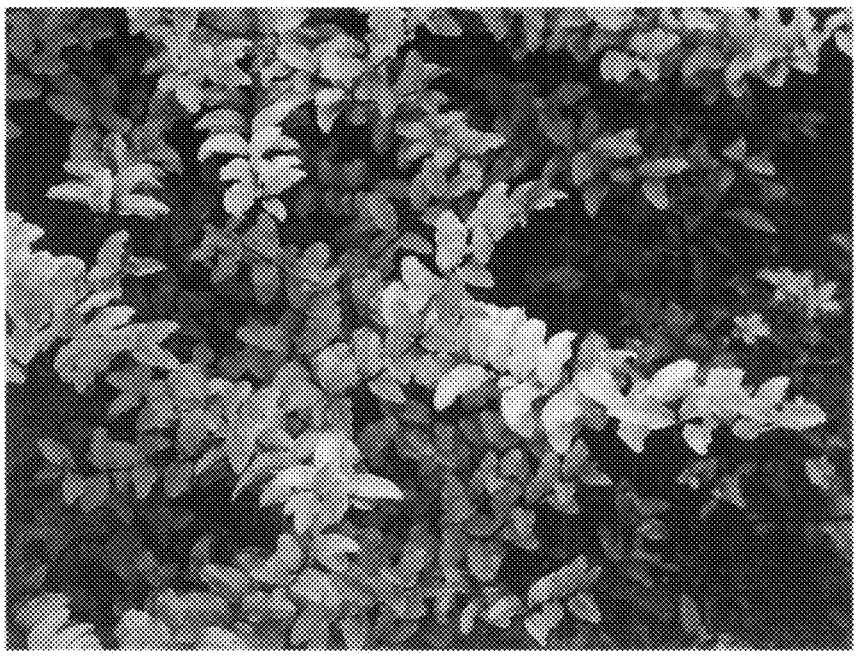
FIG. 2 illustrates a close-up view of leaves of 'Sunshine'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined under natural light conditions.

The following descriptions and measurements describe the initial selected cultivar Sunshine. The plant size and description are based on plants grown for approximately 5 years in Zebulon, N.C.

Botanical classification: *Ligustrum sinense* cultivar Sunshine.

Parentage:

*Parent.*—*Ligustrum sinense.*

Propagation:

*Type cutting.*—Terminal stem.

*Time to initiate roots.*—Approximately 10 to 15 days.

*Time to produce a rooted cutting.*—Approximately 20 to 30 days.

*Root description.*—Fibrous.

*Rooting habit.*—Freely branching.

Plant description:

*Commercial crop time.*—Approximately 4 to 8 weeks from a rooted cutting to a finished 5 cm pot.

*Growth habit and general appearance.*—Semi-evergreen to evergreen shrub. Compact habit compared to species.

*Growth rate.*—0.1 m to 0.3 m per year.

*Hardiness.*—USDA zone 7A.

*Size.*—Height from soil level to top of plant plane: Approximately 1.2 m to 1.5 m. Width: Approximately 1.2 m to 1.5 m.

*Branching habit.*—Quantity of branches per plant: 9 main branches with greater than 50 lateral branches. Freely branching, pinching enhances basal branching.

*Lateral branches.*—Shape: Round. Strength: Moderate. Length: Approximately 30 cm. Diameter: Approximately 3.5 cm. Length of central internode: 1.3 cm. Texture: New growth has downy pubescence, mature stems have glandular pubescence. Color of young stem: 166A. Color of mature stem: N199A.

Foliage description:

*General description.*—Fragrance: None. Form: Elliptic-oblong. Arrangement: Opposite.

*Leaves.*—Aspect: Petiole is at acute angle to stem and leaf blade perpendicular to stem. Shape: Elliptic-oblong. Margin: Smooth, entire with undulation. Apex: Acute to rounded occasionally retuse. Base: Attenuate. Venation pattern: Pinnate. Length of mature leaf: Approximately 3.0 cm. Width of mature leaf: Approximately 1.6 cm. Texture of upper and lower surfaces: Glabrous. Color of upper surface of summer foliage: 146A fading with full sun exposure to closest to 14A, and with venation indistinguishable from the color of the remainder of the leaf surface. Color of lower surface of summer foliage: 17D with venation indistinguishable from the color of the remainder of the leaf surface. Color of upper surface of winter foliage: Closest to 146A with venation indistinguishable from the color of the remainder of the leaf surface. Color of lower surface of winter foliage: Closest to 146C and 146B with venation indistinguishable from the color of the remainder of the leaf surface.

*Petiole.*—Length: Approximately 3.0 mm. Diameter: Less than 1 cm. Texture: Glabrous. Color: 137C fading with sun exposure to closest to 9B and with venation indistinguishable from the color of the remainder of the leaf surface.

Flowering description: No flowers have been observed.

Disease and pest resistance: Resistance to pathogens and pests common to *Ligustrum* has not been observed.

What is claimed is:

1. A new and distinct cultivar of *Ligustrum* plant named 'Sunshine', substantially as herein shown and described.

* * * * *